United States Patent [19]

Cahen

[11] 4,317,924

[45] Mar. 2, 1982

[54] PROCESS FOR PRODUCING PURIFIED TEREPHTHALIC ACID

[75] Inventor: Raymond M. Cahen, Brussels, Belgium

[73] Assignee: Labofina S.A., Brussels, Belgium

[21] Appl. No.: 143,141

[22] Filed: Apr. 23, 1980

Related U.S. Application Data

[63] Continuation of Ser. No. 7,286, Jan. 29, 1979, abandoned.

[30] Foreign Application Priority Data

Feb. 8, 1978 [GB] United Kingdom ............... 05091/78

[51] Int. Cl.$^3$ ............................................ C07C 51/42
[52] U.S. Cl. .................................................. 562/487
[58] Field of Search ........................................ 562/487

[56] References Cited

U.S. PATENT DOCUMENTS 3,456,001 7/1969 Olsen ................................... 562/487
3,607,921 9/1971 Stancell ............................... 562/487

*Primary Examiner*—Alan Siegel

[57] ABSTRACT

A process for purifying crude terephthalic acid is disclosed which comprises treating a solution of crude terephthalic acid in an aqueous solution of a water-soluble heavy metal salt wherein the heavy metal is cobalt, manganese, iron or nickel under elevated pressure and at elevated temperature in the presence of a supported noble metal catalyst with nitrogen gas or a gas-mixture of nitrogen and hydrogen. The treated solution is then separated from the catalyst and purified crystalline terephthalic acid is recovered by crystallization and separation from the mother liquor wherein impurities and the heavy metal salts are retained. The process is especially useful for directly treating crude terephthalic acid obtained in an oxidation process in the presence of a heavy-metal-salt-catalyst.

12 Claims, No Drawings

PROCESS FOR PRODUCING PURIFIED TEREPHTHALIC ACID

This is a continuation of application Ser. No. 7,286, filed Jan. 29, 1979, now abandoned.

BACKGROUND OF THE INVENTION

This invention relates to a process for the purification of crude terephthalic acid which is contaminated with reducible impurities in order to obtain a very pure fiber-grade acid.

Usually, terephthalic acid is produced by a liquid phase oxidation of p-xylene and/or p-toluic acid. Terephthalic acid is of great commercial importance and is widely used for the production of various different polymers, such as fiber-forming polyesters. A process for preparing polyesters of terephthalic acid, particularly polyethylene terephthalate, comprises a direct condensation of terephthalic acid with the respective polyalcohol, for example, terephthalic acid is reacted with ethylene glycol to form bis-($\beta$-hydroxyethyl) terephthalate which is then polymerized in a second stage. This direct condensation process is simpler than other known methods such as transerterification of dimethyl terephthalate with the appropriate glycol. However, the direct esterification requires the use of highly purified terephthalic acid. In order to be suitable for the production of polyester fibers, terephthalic acid must be substantially free of any contaminants which lower the melting point of the polyester and/or cause coloration of the polyester. In fact, some impurities which are contained in crude terephthalic acid are color-forming precursors of the terephthalic acid.

All these ipurities have not yet been identified, however 4-carboxybenzaldehyde which is an intermediate oxidation product and which in the following is abbreviated as 4-CBA, generally is found in crude terephthalic acid. It is known that the degree to which coloration in the polyester is induced is less if the 4-CBA-content of the terephthalic acid is low. While pure 4-CBA itself does not necessarily promote coloring during polymerization, this impurity is a convenient tracaer for evaluating the degree to which terephthalic acid has been refined. A process which can reduce the 4-CBA-content of terephthalic acid reduces also the content in color-forming precursors.

From the U.S. Pat. No. 3,584,039 it is known that fiber-grade terephthalic acid may be prepared by purifying crude terephthalic acid by means of a reduction procedure. The process is essentially comprised of treating an aqueous solution of crude terephthalic acid with hydrogen in the presence of a supported or unsupported Group VIII noble metal catalyst, whereby the metal and the support are insoluble in the solution under the working conditions. By this process, the amounts of 4-CBA and other coloring impurities contained in terephthalic acid are reduced under formation of removable products. Purified terephthalic acid is then recovered by crystallization, filtration and drying.

The development of the process for producing polyesters by direct condensation of terephthalic acid with ethylene glycol depends largely on the purity and price of the acid. There is thus a need for a purification process which produces very pure terephthalic acid and which can be carried out in a more economical manner than the previously used methods.

SUMMARY OF THE INVENTION

It is an object of the present invention to provide a process for purifying crude terephthalic acid by means of which terephthalic acid of fiber-grade purity is obtained.

It is a further object of the present invention to provide such a process by means of which a crude terephthalic acid, which is obtained by oxidyzing p-xylene, p-toluic acid or partially oxidized p-xylene derivatives in a liquid phase oxidation process in the presence of heavy metal salt catalysts and comprises residual amounts of heavy metal salts and of only partially oxidized products, can be treated directly without any additional purification of the crude product or elimination of the heavy metal impurities.

In order to accomplish the foregoing objects, according to the present invention there is provided a process for preparing purified terephthalic acid from crude terephthalic acid which is contaminated by impurities capable of undergoing reduction-oxidation reactions, e.g., 4-CBA, which comprises the steps of:

(a) preparing an aqueous reaction mixture comprising the crude terephthalic acid substantially suspended in an aqueous solution of a reduction-oxidation-reaction-enhancing amount of a water-soluble salt of a heavy metal selected from the group consisting of cobalt, manganese, iron, nickel and mixtures thereof;

(b) treating the aqueous reaction mixture in the presence of a catalyst comprising a noble metal of Group VIII of the Periodic System, preferably palladium, on a catalyst support which is substantially insoluble in the reaction mixture, with a gas which is nitrogen or a mixture of nitrogen and hydrogen having a sufficiently low partial hydrogen pressure to essentially not cause reduction of the terephthalic acid, at a sufficiently elevated reaction temperature to maintain the terephthalic acid substantially dissolved in the aqueous solution, and under a sufficiently elevated total pressure to maintain the aqueous solution in a liquid phase; and (c) recovering purified terephthalic acid from the reaction mixture.

The above-defined process is particularly useful for purifying crude terephthalic acid which is obtained by means of liquid phase oxidation of p-xylene, p-toluic acid and partially oxidized p-xylene derivatives with molecular oxygen in the presence of water and a heavy metal salt catalyst. In this case at least part of the amount of the water-soluble salt of the heavy metal is comprised of residual heavy metal salt catalyst in the crude terephthalic acid.

Further objects, features and advantages of the invention will become apparent from the detailed description of the invention and its preferred embodiments which follows:

DETAILED DESCRIPTION OF THE INVENTION AND ITS PREFERRED EMBODIMENTS

It has been found that terephthalic acid with an unexpectedly low content in 4-CBA and other color-forming precursors is obtained by using the process of this invention. Moreover, this result is obtained without any preliminary purification treatment of the crude terephthalic acid even when the treated crude terephthalic acid has a high content in 4-CBA, which may exceed 2% by weight or 20,000 ppm by weight. Furthermore, this process is very efficient and the period of time required for purifying terephthalic acid is shorter than in other processes. Very pure terephthalic acid can therefore be produced in a more economical way.

The amount of water-soluble heavy metal salt may be so low as to comprise about 25 ppm by weight of the heavy metal relative to the weight of dry crude terephthalic acid, and valuable results are already obtained with an amount of heavy metal of about 20 ppm or even less. Advantageously, the amount of soluble heavy metal salt may vary and may be equivalent to an amount of metal of from about 25 to about 1,000 ppm relative to the weight of dry crude terephthalic acid. Amounts higher than 1,000 ppm can be used but without further improving the results. Excellent results have been obtained with amounts of heavy metal of from about 50 to about 100 ppm. Any salt of the heavy metal with an organic acid which is soluble in the aqueous solution of crude terephthalic acid or any heavy metal compound which is capable of forming a soluble salt in said solution and which does not react with the noble metal catalyst may be used. Suitable salts are salts of lower aliphatic carboxylic acids, such as acetates, propionates, butyrates and mixtures thereof which the heavy metals such as cobalt, manganese, iron, nickel and mixtures thereof. It has been observed that the salts of these heavy metals can be substantially completely removed from the obtained purified terephthalic acid by washing the latter with water.

The impure terephthalic acid is contacted with a gas which may be a mixture of hydrogen and nitrogen or nitrogen alone. The process of the invention is so efficient that the use of hydrogen alone or of mixtures of hydrogen and nitrogen having a high partial pressure of hydrogen could result in a hydrogenation of terephthalic acid into cyclohexane dicarboxylic acid. When used in admixture with nitrogen, hydrogen is preferably employed in an amount corresponding to the stoichiometric amount which is necessary to reduce the 4-CBA-content or in an amount which is slightly, e.g., about 10 to 25%, in excess of this stoichiometrically required amount.

The Group VIII noble metal within the reduction-catalyst may be ruthenium, rhodium, palladium, osmium, irridium, platinum or a mixture or an alloy thereof. Excellent results are obtained by using palladium. The noble metal is generally supported by a support material which is insoluble in the aqueous terephthalic acid solution. Particularly suitable inert support materials are carbon and/or charcoal. The amount of noble metal in a support noble metal catalyst may vary from about 0.1 to about 5 percent by weight and preferably is from about 0.25 to about 1 percent by weight, relative to the total weight of the support and the noble metal.

The suitable reaction temperature at which the process of the invention is carried out may vary depending on the concentration of the aqueous solution of terephthalic acid. Advantageously, an aqueous solution which is treated in the process contains aout 10% by weight of impure terephthalic acid and the substantial part of this acid is dissolved in water. Therefore, the process is suitably carried out at a temperature of at least about 240° C. and which suitably does not exceed about 300° C. The pressure must be sufficiently high so that the aqueous solution is maintained in the liquid phase at these temperatures. Higher concentrations of terephthalic acid may be used at higher temperatures, up to the critical temperature of water (374° C.).

The process of this invention can be used to purify terephthalic acid obtained from any source. It is advantageously used for the purification of terephthalic acid which has been prepared in the oxidation process described in the U.S. patent applications, Ser. Nos. 764,981, 785,827, and 947,641, the disclosures of which are hereby included by reference. According to this process for the liquid phase oxidation of p-xylene and p-toluic acid with molecular oxygen in the presence of a catalytic amount of at least one heavy metal, the oxidation is carried out in the presence of water as solvent and of p-toluic acid. Thus, the main advantages of this process are that no solvent other than water and no promoter are used in this oxidation step, whereas previously employed oxidation processes use acetic acid as a solvent and bromine or brominated compounds as promoters. The crude terephthalic acid obtained by this method has a low content of colored by-products. When the process of the present invention is used to refine the so-prepared crude terephthalic acid, no preliminary purification step is required as the resulting purified acid meets the high standards of purity which are required in the production of polyesters by direct condensation with diols. Advantageously, the crude terephthalic acid is dissolved in an aqueous solution of the heavy metal salt at a temperature and a pressure sufficiently high to provide a substantially complete dissolution and to maintain the resulting solution in the liquid phase. The solution is subjected to the treatment with the gas in the presence of the noble metal catalyst under the elevated temperature and pressure, e.g., in the manner disclosed in U.S. Pat. No. 3,584,039, the disclosure of which is hereby incorporated by reference, and then is separated from the noble metal catalyst. After separating the reaction solution from the catalyst, crystallization of the terephthalic acid is advantageously effected by releasing the pressure whereby water is evaporated from the solution, the solution is simultaneously cooled and precipitation of crystalline terephthalic acid takes place. The crystalline terephthalic acid is separated from the mother liquor, e.g., by filtration centrifugation. The resulting crystals of purified terephthalic acid may further be washed with water to remove adherent mother liquor therefrom, and then dried.

The following non-limitative examples are given to further illustrate the invention.

EXAMPLE 1

In several experiments crude terephthalic acid is purified in the presence of various amounts of different water-soluble heavy metal salts. In each experiment, 50 g of crude terephthalic acid containing 2.2% by weight of 4-CBA are dissolved in 500 g $H_2O$. A supported palladium catalyst (0.5% by weight Pd on charcoal) is added in an amount corresponding to 1% by weight relative to the weight of the aqueous solution. Furthermore, soluble heavy metal salts are added in the amounts given in the Table I below.

The solutions are treated with a gas mixture containing 90% vol. of $N_2$ and 10% vol. of $H_2$ at a temperature of 255±5° C., and under pressure of 47.5±2.5 kg/cm$^2$, under stirring at a stirring rate of 1900 rpm for a period of 3 hours. Thereafter, the supported noble metal catalyst is filtered off, the pressure is released and the filtrate is allowed to cool to room temperature whereby crystalline purified terephthalic acid precipitates. The crystalline terephthalic acid is separated from the mother liquor. The amounts of residual 4-CBA and heavy metal in the resulting purified acid are determined.

The following results are obtained.

TABLE I

| Experiment No. | Soluble heavy metal salt Type | Amount* | Amount of residual 4-CBA in purified acid** | % by weight conversion* of 4-CBA |
|---|---|---|---|---|
| 1 | None | — | 110 | 99.50 |
| 2 | Co acetate | 68 | 13 | 99.94 |
| 3 | Co + Mn acetates | 75 + 25 | 4 | 99.98 |
| 4 | Fe propionate | 82 | 3 | 99.99 |
| 5 | Mn toluate | 30 | 20 | 99.91 |
| 6 | Mn acetate | 100 | 15 | 99.93 |
| 7 | Ni acetate | 86 | 3 | 99.99 |

*in ppm of heavy metal based on dry crude feed;
**in ppm based on dry purified terephthalic acid.

In each case (Experiments 2 to 7), the amount of heavy metal in the crystallized pure terephthalic acid was lower than 1 ppm, the added heavy metal salt is retained in the mother liquor.

The results of these experiments clearly show that very pure terephthalic acid can be obtained when the crude acid is treated in the presence of a water-soluble salt of cobalt, manganese, iron, nickel or a mixture thereof which is added to the aqueous solution of crude acid.

EXAMPLE 2

50 g of crude terephthalic acid (prepared according to the process described in applications Ser. Nos. 764,981, 785,827 and 947,641 are dissolved in 500 g $H_2O$. This crude terephthalic acid contains 2 wt.% of 4-CBA and also soluble organic salts of cobalt, manganese and iron in respective amounts corresponding to 68 ppm, 26 ppm, and 55 ppm of metal based on dry acid. A supported palladium catalyst (0.5% by weight Pd on charcoal) is added in an amount corresponding to 1% by weight, relative to the weight of the aqueous solution.

The solution is treated with nitrogen under a temperature of 255°±5° C. and under a pressure of 47.5±2.5 kg/cm², under stirring at a stirring rate of 1900 rpm for a period of 3 hours at reaction temperature.

The resulting purified terephthalic acid contains 37 ppm of 4-CBA.

EXAMPLE 3

The experiment described in Example 2 is repeated, but the solution is treated with a gas containing 90 vol. % of $N_2$ and 10 vol. % of $H_2$.

The resulting purified terephthalic acid contains 2 ppm of 4-CBA.

What is claimed is:

1. A process for producing purified terephthalic acid from crude terephthalic acid which is contaminated by impurities capable of undergoing reduction-oxidation reactions, which comprises the steps of:
  (a) preparing an aqueous reaction mixture comprising the crude terephthalic acid suspended in an aqueous solution of a reduction-oxidation-reaction-enhancing amount of a water-soluble salt of a heavy metal selected from the group consisting of cobalt, manganese, iron, nickel and mixtures thereof wherein the reduction-oxidation-reaction-enhancing amount is an amount from about 25 to about 1000 ppm by weight of heavy metal relative to the weight of dry crude terephthalic acid;
  (b) treating the aqueous reaction mixture in the presence of a catalyst comprising a noble metal of Group VIII of the Periodic System on a catalyst support which is substantially insoluble in the reaction mixture with a gas, which comprises nitrogen or a mixture of nitrogen and hydrogen having a sufficiently low partial hydrogen presshre to essentially not cause reduction of the terephthalic acid, at a sufficiently elevated reaction temperature to maintain the terephthalic acid substantially dissolved in the aqueous solution, and under a sufficiently elevated total pressure to maintain the aqueous solution in a liquid phase; and
  (c) recovering purified terephthalic acid from the reaction mixture.

2. The process as defined in claim 1, wherein the Group VIII noble metal is palladium.

3. The process as defined in claim 2, wherein the amount of water-soluble heavy metal salt is equivalent to from about 50 to about 100 ppm by weight of heavy metal relative to the weight of dry crude terephthalic acid.

4. The process as defined in claim 1, wherein the gas is a mixture of nitrogen and hydrogen comprising an amount of hydrogen not substantially in excess of the stoichiometric amount which is necessary to reduce 4-carboxybenzaldehyde contained in crude terephthalic acid.

5. The process as defined in claim 1, wherein the water-soluble heavy metal salt is selected from the group consisting of heavy metal acetates, -proprionates, -butyrates and mixtures thereof.

6. The process as defined in claim 1, wherein the reaction temperature is from about 240° C. to about 300° C.

7. The process as defined in claim 2, wherein in step (b) the reaction temperature is from about 250° C. to about 260° C. and the total pressure is from about 45 to about 50 kg/cm².

8. The process as defined in claim 1, wherein step (c) comprises the steps of:
  ($c_1$) separating the aqueous solution from the noble metal-comprising catalyst at a sufficiently elevated reaction temprature to maintain the terephthalic acid substantially dissolved in the aqueous solution, and under a sufficiently elevated pressure to maintain the aqueous solution in a liquid phase;
  ($c_2$) sufficiently cooling the separated aqueous solution and releasing the elevated pressure in order to obtain a precipitate of crystalline purified terephthalic acid in a mother liquor; and
  ($c_3$) separating the purified terephthalic acid from the mother liquor.

9. The process as defined in claim 1, wherein the crude terephthalic acid is a crude terephthalic acid obtained by means of liquid phase oxidation of p-xylene, p-toluic acid and partially oxidized p-xylene derivatives with molecular oxygen in the presence of water and a heavy-metal-salt catalyst, and wherein at least part of the amount of the water-soluble salt of the heavy metal is comprised of residual heavy-metal-salt-catalyst in the crude terephthalic acid.

10. The process as defined in claim 9, which comprises the steps of:
  ($a_1$) oxidizing a substantially liquid reaction mixture comprising at least one oxidizable terephthalic acid precursor selected from the group consisting of p-toluic acid, and mixtures of p-toluic acid and an oxidizable compound selected from the group of p-xylene, partially oxidized p-xylene derivatives, and mixtures thereof; and an amount of at least 5% by weight of water which is sufficient to obtain a workable slurry with a molecular oxygen-containing gas in the presence of an oxidation catalyst which comprises at least one heavy metal salt selected from the group consisting of salts of cobalt, manganese and mixtures thereof at oxidation conditions sufficient to form an oxidizing reaction mixture comprising terephthalic acid;

($a_2$) separating from said oxidized mixture solid crude terephthalic acid at a temperature sufficient to substantially maintain other components of the oxidized mixture in a liquid solution, whereby a crude terephthalic acid product comprising residual amounts of the heavy metal salt is obtained; and ($a_3$) substantially dissolving the crude terephthalic acid product in water to obtain the aqueous reaction mixture.

11. The process as defined in claim 1, wherein said step of preparing an aqueous reaction mixture comprises combining the crude terephthalic acid, water and an amount of said heavy metal salt sufficient to produce said reduction-oxidation-reaction enhancing amount.

12. The process as defined in claim 11, wherein the crude terephthalic acid is added to an aqueous solution of said heavy metal.

* * * * *